United States Patent [19]
Hewawasam et al.

[11] Patent Number: 6,034,113
[45] Date of Patent: Mar. 7, 2000

[54] DERIVATIVES OF 1,3,4-OXADIAZOLONE

[75] Inventors: Piyasena Hewawasam, Middletown; Min Ding, Glastonbury; John E. Starrett, Jr., Middletown, all of Conn.

[73] Assignee: Bristol-Myers Squibb Company, Princeton, N.J.

[21] Appl. No.: 09/232,033

[22] Filed: Jan. 15, 1999

Related U.S. Application Data

[60] Provisional application No. 60/102,274, Sep. 29, 1998, and provisional application No. 60/072,966, Jan. 29, 1998.

[51] Int. Cl.[7] ....................... C07D 271/113; A61K 31/41
[52] U.S. Cl. ............................................. 514/364; 548/144
[58] Field of Search .............................. 548/144; 514/364

[56] References Cited

U.S. PATENT DOCUMENTS 3,971,803  7/1976  Rosenberger et al. .
5,869,509  2/1999  Romine et al. .

FOREIGN PATENT DOCUMENTS 533 276      3/1993  European Pat. Off. .
WO 93/08800  5/1993  WIPO .
WO 98/04135  2/1998  WIPO .

OTHER PUBLICATIONS

Ahmed, F. et al., "Some Features of the Spasmogenic Actions of Acetylcholine and Histamine in Guinea–Pig Isolated Trachealis", *Br. J. Pharmacol.*, 83, pp. 227–233 (1984).

Baró, I. and Escande, D., "A $Ca^{2+}$–activated $K^+$ Current in Guinea–pig Atrial Myocytes", *Pflügers Archiv.*, 414 (Suppl. 1), p. S168–S–170 (1989).

Cook, N.S., "The Pharmacology of Potassium Channels and Their Therapeutic Potential", *Trends in Pharmacol. Sciences*, 9, pp. 21–28 (Jan., 1988).

Koh, D–S., et al., "Effect of the Flavoid Phloretin on $Ca^{2+}$–activated $K^+$ Channels in Myelinated Nerve Fibres of *Xenopus Laevis*", *Neuroscience Lett.* 165, pp. 167–170 (1994).

Quast, U. and Cook, N. S, "Moving Together: $K^+$ Channel Openers and ATP–sensitive $K^+$ Channels", *Trends in Pharmacol. Sciences*, 10, pp. 431–435 [Nov., 1989).

Singer, J. J. and Walsh, J.V., "Characterization of Calcuim–activated Potassium Channels in Single Smooth Muscle Cells Using the Patch–clamp Technique", *Pflügers Archiv.*, 408, pp. 98–111 (1987).

Trivedi, S., et al., "Calcium Dependent K–Channels In Guinea Pig and Human Urinary Bladder", *Biochemical and Biophysical Research Communications*, 213, No. 2, pp. 404–409 (Aug., 1995).

Wilder Smith, A.E., "Preparation of Some New 4–Substituted Derivatives of p–Amino–o–hydroxy–phenyl–1,3, 4–oxadiazolone–5 and Study of their Mycobacteriostatic Activity", *Arzneim. Forsch.*, 67, No. 17, p. 768–72 (1967).

*Primary Examiner*—Robert Gerstl
*Attorney, Agent, or Firm*—Aldo A. Algieri

[57] ABSTRACT

The present invention provides novel oxadiazolone derivatives having the general formula

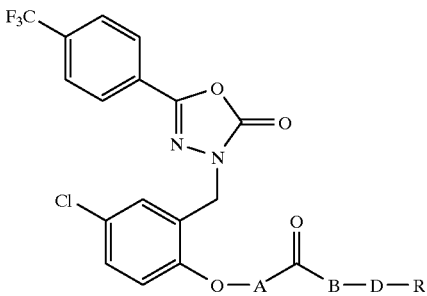

wherein A, B, D and R are as defined herein, or a nontoxic pharmaceutically acceptable salt or solvate thereof and are useful in the treatment of disorders which are responsive to the opening of the large conductance calcium-activated potassium channels.

16 Claims, No Drawings

DERIVATIVES OF 1,3,4-OXADIAZOLONE

CROSS-REFERENCE TO RELATED APPLICATIONS

This is a nonprovisional application which claims the benefit of provisional applications, U.S. Ser. No. 60/102,274 filed Sep. 29, 1998, and U.S. Ser. No. 60/072,966 filed Jan. 29, 1998.

FIELD OF THE INVENTION

The present invention is directed to novel derivatives of a 1,3,4-oxadiazol-2(3H)-one compound which is a modulator of the large-conductance calcium-activated potassium (BK) channels and, therefore, useful in the protection of neuronal cells and diseases arising from dysfunction of cellular membrane polarization and conductance. The present invention also provides a method of treatment with the novel substituted oxadiazolone derivatives and to pharmaceutical compositions thereof.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences*, 9, pp. 21–28 (1988); and Quast, U. and Cook, N. S., *Trends in Pharmacol. Sciences*, 10, pp. 431–435 (1989)]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.*, 408, pp. 98–111 (1987); Baró, I., and Escande, D., *Pflügers Archiv.*, 414 (Suppl. 1), pp. S168–S170 (1989); and Ahmed, F. et al., *Br. J. Pharmacol.*, 83, pp. 227–233 (1984)].

Potassium ions play a dominant role in controlling the resting membrane potential in most excitable cells and in maintaining the transmembrane voltage near the $K^+$ equilibrium potential ($E_k$) of about −90 mV. It has been shown that opening of potassium channels shifts the cell membrane potential towards the equilibrium potassium membrane potential ($E_k$), resulting in hyperpolarization of the cell. [Cook, N. S., *Trends in Pharmacol. Sciences*, 9, pp. 21–28 (1988]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications*, (1995), 213, No.2, pp. 404–409.

A range of synthetic and naturally occurring compounds with BK opening activity have been reported. The avena pyrone extracted from avena sativa-common oats has been identified as a BK channel opener using a lipid bi-layer technique [International Patent application WO 93/08800, published May 13, 1993]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.*, 165, pp.167–170 (1994)].

U.S. Pat. No. 3,971,803 issued to S. Rosenberger and K. Schwarzenbach on Jul. 27, 1976, relates to compounds of Formula (i):

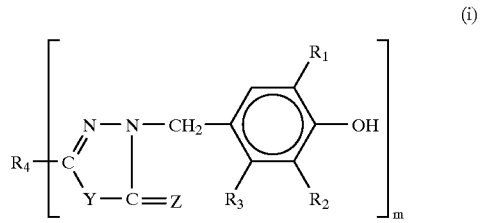

wherein $R_1$ is alkyl, cycloalkyl or aralkyl;

$R_2$ is hydrogen or $R_1$;

$R_3$ is hydrogen or $C_{14}$ alkyl;

Y and Z are independently O or S;

$R_4$ is either (1), if m=1, $C_{1-8}$ alkylene, —$C_xH_{2x}$—Q—$C_yH_{2y}$— (Q is O or S, x and y are integers whose sum is 2 to 4), phenylene, diphenylene or naphthalene or a

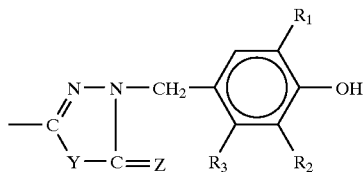

group;

or (2) if m=2, alkylene, alkylene ether, alkylene thioether, diphenylene, or napthalene. The compounds are antioxidants for organic polymers.

EPO 0-533276-A1 published on Mar. 24, 1993, shows compounds of Formula (ii):

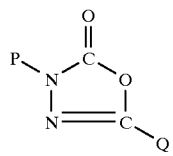

wherein one of P or Q is an ortho-substituted phenyl group and the other a substituted benzyl. The Formula (ii) compounds are miticides and insecticides.

A. E. Wilder Smith disclosed in *Arzneim. Forsch.* (1967) 67, No. 17, pp. 768–772, the preparation and study of compounds of Formula (iii):

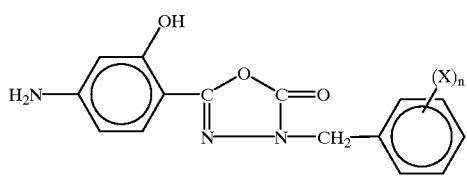

wherein X is H or Cl and n is 1 or 2. The compounds have tuberculostatic properties. Formula (iii) compounds do not encompass substitution para to the hydroxyl group.

J. L. Romine, et al. in International Patent Application WO 98/04135, published Feb. 5, 1998, describe a series of diphenyl heterocycles of the Formula (iv):

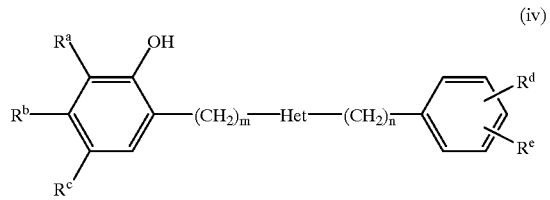

wherein Het is a heterocyclic moiety selected from inter alia, oxadiazolone. The compounds are useful as modulators of the large conductance calcium-activated potassium channels and the starting material for the preparation of the compounds of the present invention is described therein wherein Het is 1,3,4-oxadiazol-2(3H)-one, m=1 and n=0, $R^c$ is chloro, $R^d$ is trifluoromethyl and $R^a=R^b=R^e$ is hydrogen.

None of these references teach or suggest the novel compounds of the present invention.

SUMMARY OF THE INVENTION

The present invention provides novel derivatives of 1,3,4-oxadiazolone having the general formula

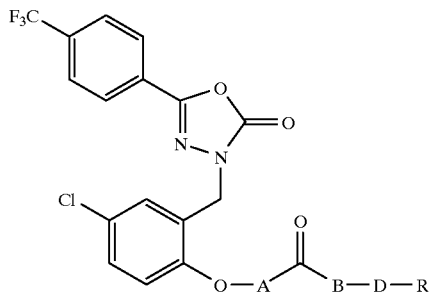

wherein A, B, D and R are as defined below, or a nontoxic pharmaceutically acceptable salt or solvate thereof. The present invention also provides pharmaceutical compositions comprising said derivatives and to the method of treatment of disorders sensitive to potassium channel opening activity such as ischemia, stroke, convulsions, epilepsy, asthma, irritable bowel syndrome, migraine, traumatic brain injury, spinal cord injury, sexual dysfunction, and urinary incontinence.

DETAILED DESCRIPTION OF THE INVENTION

The present invention provides novel derivatives of 3-[(5-chloro-2-hydroxyphenyl)methyl]-5-[4-(trifluoromethyl)phenyl]-1,3,4-oxadiazol-2(3H)-one which is a potent opener of the large conductance, calcium-activated $K^+$-channels (BK channel) and the novel derivatives have the general Formula

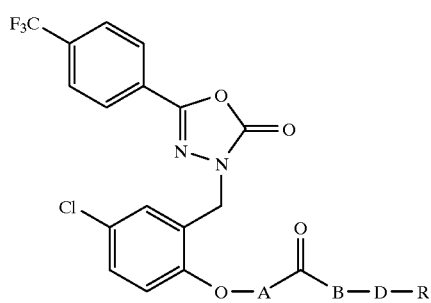

wherein
A is a direct bond or —$CH_2O$—;
B is a direct bond or oxygen;
D is —$(CH_2)_n$— or —$CH_2CHOHCH_2$—;
n is an integer from 1 to 4;
R is —$NR^1R^2$ or

in which $\overset{\ominus}{X}$ is a counter anion; and
$R^1$, $R^2$, and $R^3$ each are independently hydrogen or $C_{1-4}$ alkyl;
or a nontoxic pharmaceutically acceptable salt or solvate thereof.

The present invention also provides a method for the treatment of or protection from disorders which are mediated by opening of the large conductance calcium-activated K⁺ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, stroke, epilepsy, convulsions, asthma, irritable bowel syndrome, migraine, traumatic brain injury, spinal cord injury, sexual dysfunction, and urinary incontinence and other disorders sensitive to BK channel activating activity.

The term "$C_{1-4}$ alkyl" as used herein and in the claims (unless the context indicates otherwise) means straight or branched chain alkyl groups such as methyl, ethyl, propyl, isopropyl, butyl. Preferably, these groups contain from 1 to 2 carbon atoms.

The term "a nontoxic pharmaceutically acceptable salt" and "counter anion" as used herein and in the claims is intended to include nontoxic acid addition salts and counter anions with inorganic and organic acids. Suitable salts with an acid and/or suitable counter anions of an acid are intended to include inorganic acid salts such as hydrochloride, hydrobromide, hydroiodide, sulfate, phosphate, and the like, and organic acid salts and/or counter anions of an acid such as formate, acetate, maleate, citrate, succinate, ascorbate, lactate, fumarate, methanesulfonate and tartrate which have been used to form salts of basic amines and quaternary amines.

As the compounds of the present invention may possess an asymmetric carbon atom, the present invention is intended to include the racemate as well as the individual enantiometric forms of the compounds of Formula I as described herein and in the claims, e.g., the (D), (L) and (DL) forms of norcamitine and camitine.

Generally, pharmaceutically acceptable salts of the invention are those in which the counter anion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound with the selected acid, preferably by contact in solution employing an excess of commonly used inert solvents such as water, ether, dioxane, methylene chloride, isopropanol, methanol, ethanol, ethyl acetate and acetonitrile. They may also be made by metathesis or treatment with an ion exchange resin under conditions in which the appropriate ion of a salt of the substance of the Formula I is replaced by another ion under conditions which allow for separation of the desired species such as by precipitation from solution or extraction into a solvent, or elution from or retention on an ion exchange resin.

Certain compounds of the present invention including the pharmaceutically acceptable salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated K⁺ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

In another aspect, this invention provides water-soluble prodrugs of 3-[(5-chloro-2-hydroxyphenyl)methyl]-5-[4-(trifluoromethyl)phenyl]-1,3,4-oxadiazol-2(3H)-one which is described in WO 98/04135. As used herein the term prodrug denotes a derivative of an active drug which is converted after administration back to the active drug. More particularly, it refers to derivatives of 1,3,4-oxadiazol-2 (3H)-one compounds which may be active drugs and/or which are capable of undergoing hydrolysis of the ester or methyleneoxy ester moiety or cleavage of the ester so as to release active free drug. The physiologically hydrolyzable groups serve as prodrugs by being hydrolyzed in the body to yield the parent drug per se, and thus, the water-soluble prodrugs of the present invention are preferred for administration of the parent drug.

In still another aspect, this invention provides a method for the treatment of or protection from disorders which are mediated by opening of the large conductance calcium-activated K⁺ channels (BK channels) in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, stroke, convulsions, epilepsy, asthma, irritable bowel syndrome, migraine, traumatic brain injury, spinal cord injury, urinary incontinence and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity. Most preferably, the compounds of Formula I are useful in the treatment of cerebral ischemia/stroke.

In still yet another aspect, this invention provides pharmaceutical compositions comprising at least one compound of Formula I in combination with a pharmaceutical adjuvant, carrier or diluent.

The compounds of Formula I may be prepared by various procedures such as those illustrated herein in the examples, in the Reaction Schemes and variations thereof which would be evident to those skilled in the art. The various prodrug compounds of Formula I may advantageously be prepared from the active drug substance of Formula II which is itself prepared by the general procedure described in WO 98/04135 and in Example I and used as the starting material in the methods illustrated in Reaction Schemes 1 to 5.

REACTION SCHEME 1

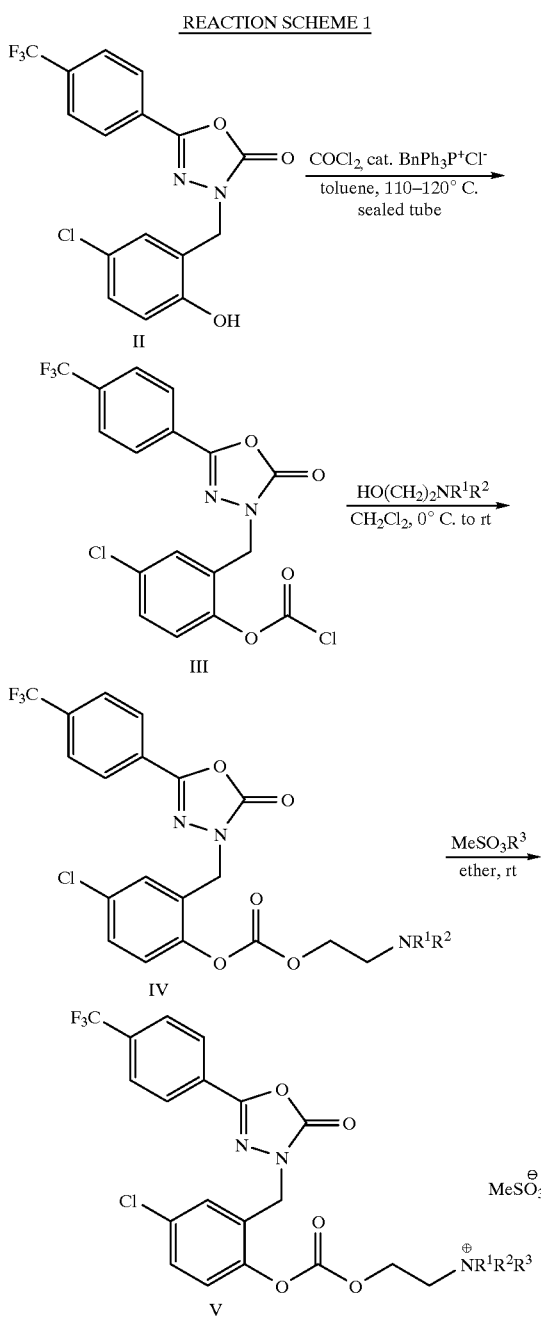

The preparation of 1,3,4-oxadiazol-2-(3H)-one derivatives of Formula V is illustrated in Reaction Scheme 1. The compound of Formula II is treated with phosgene and a catalytic amount of a phase transfer reagent such as benzyl-triphenyl phosphonium chloride in toluene and heated in a sealed tube to provide the chloroformate of Formula III which is then treated with an appropriately substituted N,N-dialkylaminoalcohol in an inert organic solvent such as methylene chloride to produce the carbonate compounds of Formula IV. When it is desired to prepare the compounds of Formula V, the amino compound of Formula IV is quaternarized with a methylating agent such as methyl methanesulfonate to produce the quaternary amine of Formula V by standard procedures well-known to those skilled in the art.

REACTION SCHEME 2

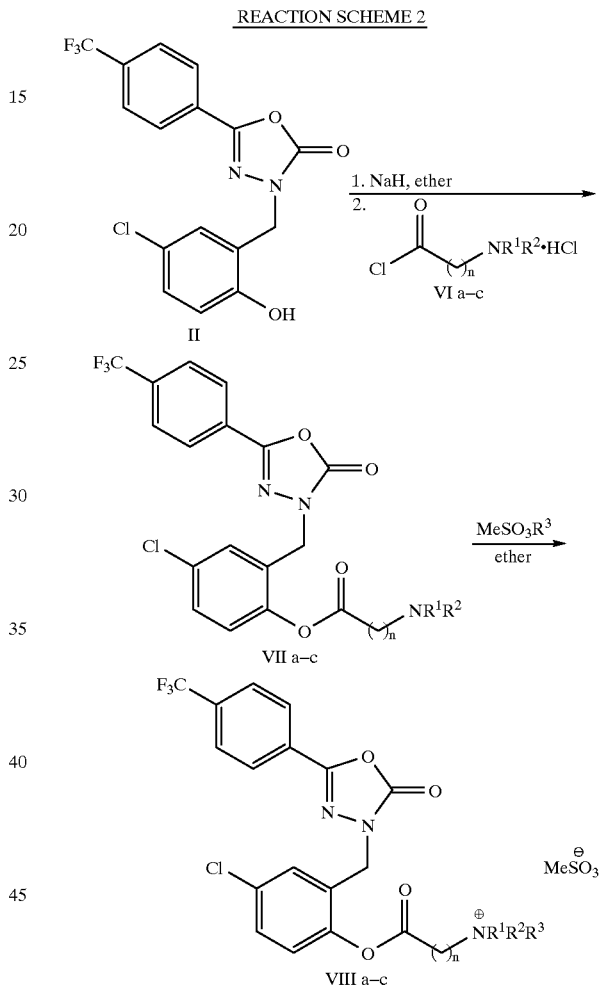

When it is desired to prepare compounds of Formula VIII wherein n is 1 to 4, the compound of Formula II is deprotonated with a base such as sodium hydride and then acylated with the desired N,N-dialkylamino acid chloride to produce the ester of Formula VII which is advantageously quaternarized with an alkylating agent such as methyl methanesulfonate to afford the quaternary amine of Formula VIII.

REACTION SCHEME 3

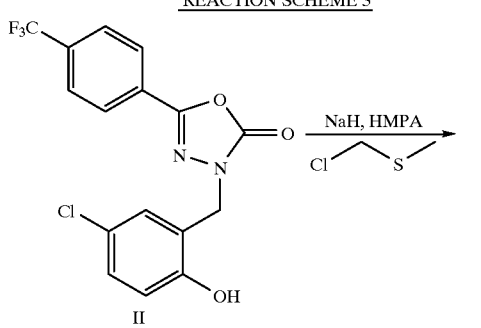

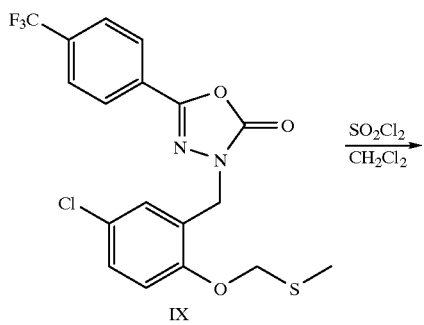

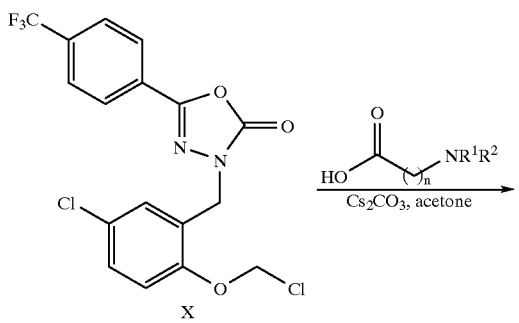

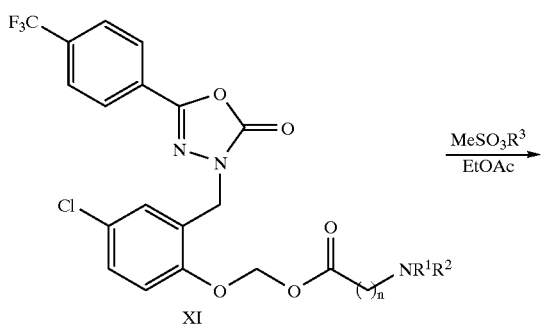

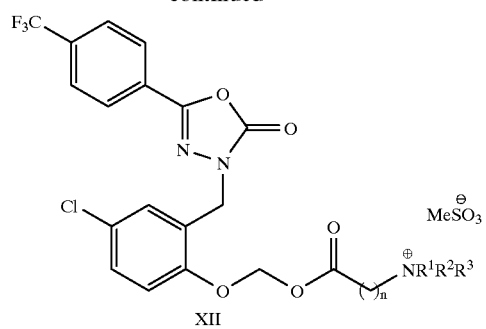

The preparation of compounds of the Formula XII is illustrated in Reaction Scheme 3 wherein $R^1$, $R^2$, $R^3$ and n are as defined herein. The compound of Formula II is deprotonated with a base such as sodium hydride and then alkylated with chloromethyl methyl sulfide to provide the thiomethylmethyl ether of Formula IX. Treatment of the compound of Formula IX with a chlorinating agent such as sulfuryl chloride yields the chloromethyl ether of Formula X which is then treated with the desired N,N-dialkylaminoacid in the presence of a base such as cesium carbonate to afford the corresponding methoxy ester of Formula XI. When it is desired to prepare the compounds of Formula XII, the amine of Formula XI is quaternarized with a methylating agent such as methyl methanesulfonate to produce the quaternary amine of Formula XII.

REACTION SCHEME 4

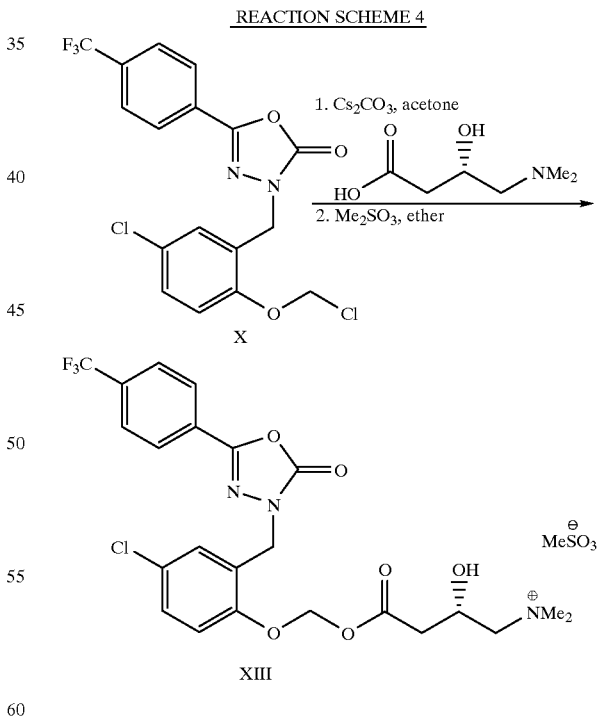

The preparation of the compound of Formula XIII is readily carried out by treating the chloromethyl ether of Formula X with carnitine in the presence of a base such as cesium carbonate and then treating the subsequent product with a methylating agent such as methyl methanesulfonate to afford the quaternary amine of Formula XIII.

REACTION SCHEME 5

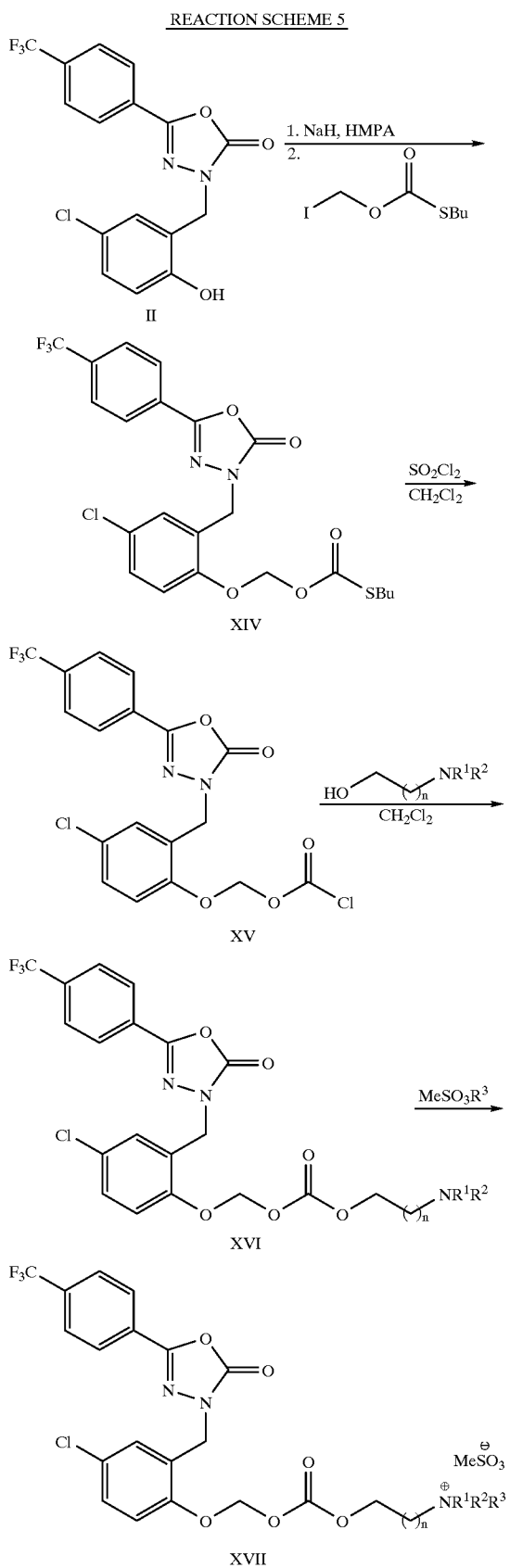

The preparation of compounds of the Formula XVII is illustrated in Reaction Scheme 5 wherein $R^1$, $R^2$, $R^3$ and n are as defined herein. The compound of Formula II is deprotonated with a base such as sodium hydride and then alkylated with iodomethyl butyl carbononothioate to give the methoxythiocarbonate of Formula XIV. Treatment of the intermediate of Formula XIV with a chlorinating agent such as sulfuryl chloride produces the chloroformate of Formula XV, which is then treated with the desired N,N-dialkylamino alcohol to give the corresponding methoxy carbonate of Formula XVI. The compounds of Formula XVI may subsequently be alkylated with a methylating agent such as methyl methanesulfonate to afford the quaternary amine of Formula XVII.

In a preferred embodiment of the invention the compounds of Formula I have the Formula Ia

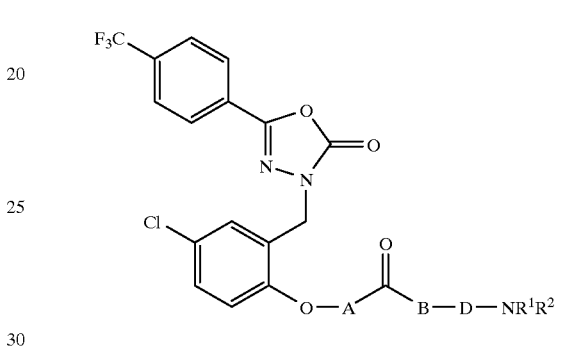

Ia wherein A is a direct bond or —$CH_2O$—; B is a direct bond or oxygen; D is —$(CH_2)_n$— or —$CH_2CHOHCH_2$— wherein n is 1 to 4; and $R^1$ and $R^2$ are hydrogen or $C_{1-4}$alkyl; or a nontoxic pharmaceutically acceptable salt or solvate thereof. More preferably, A is a direct bond or —$CH_2O$—; B is a direct bond; D is —$(CH_2)_n$— wherein n is 1, 2 or 3; and $R^1$ and $R^2$ are methyl or ethyl. It is most preferred that A is —$CH_2O$—; B is a direct bond; D is —$(CH_2)_n$— wherein n is 2 or 3; and $R^1$ and $R^2$ are methyl; or a nontoxic pharmaceutically acceptable salt or solvate thereof.

In another preferred embodiment of the invention the compounds of Formula I have the Formula Ib

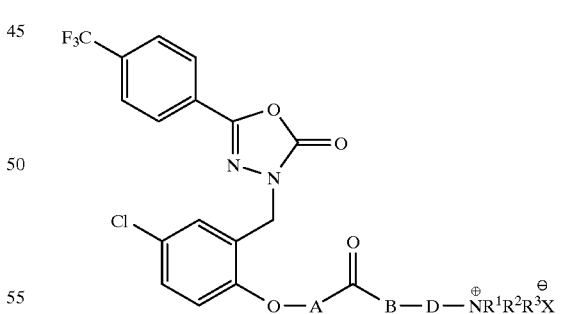

Ib wherein A is a direct bond or —$CH_2O$—; B is a direct bond or oxygen; D is —$(CH_2)_n$— or —$CH_2CHOHCH_2$— wherein n is 1 to 4; $R^1$,$R^2$ and $R^3$ are hydrogen or $C_{1-4}$alkyl; and $X^\ominus$ is a counter anion or a nontoxic pharmaceutically acceptable salt or solvate thereof. More preferably, A is a direct bond or —CH$_2$O—; B is a direct bond; D is —(CH$_2$)$_n$— wherein n is 1, 2 or 3; R$^1$, R$^2$ and R$^3$ are methyl; and

X is chloro, bromo, sulfate, phosphate or methanesulfonate. It is most preferred that A is —CH$_2$O—; B is a direct bond; D is —(CH$_2$)$_n$— wherein n is 3; R$^1$, R$^2$ and R$^3$ are methyl; and

X is methanesulfonate; or a nontoxic pharmaceutically acceptable salt or solvate thereof.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating ischemia, convulsions, epilepsy, asthma, irritable bowel syndrome, migraine, traumatic brain injury, spinal cord injury, male and female sexual dysfunction, urinary incontinence and especially stroke in a mammal in need thereof, which comprises administering to said mammal a therapeutically effective amount of a compound of Formula I or a nontoxic pharmaceutically acceptable salt, solvate or hydrate thereof.

Biological Activity

Potassium (K$^+$) channels are structurally and functionally diverse families of K$^+$-selective channel proteins which are ubiquitous in cells, indicating their central importance in regulating a number of key cell functions [Rudy, B., Neuroscience, 25 pp. 729–749 (1988)]. While widely distributed as a class, K$^+$ channels are differentially distributed as individual members of this class or as families. [Gehlert, D. R., et al., Neuroscience, 52, pp. 191–205 (1993)]. In general, activation of K$^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, K$^+$ channels can respond to important cellular events such as changes in the intracellular concentration of ATP or the intracellular concentration of calcium (Ca$^{2+}$). The central role of K$^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K$^+$ channels, the large-conductance Ca$^{2+}$-activated K$^+$ channels (BK or BK channels), is regulated by transmembrane voltage, intracellular Ca$^{2+}$, and a variety of other factors such as the phosphorylation state of the channel protein. [Latorre, R., et al., Ann. Rev. Physiol., 51, pp. 385–399 (1989)]. The large, single channel-conductance (generally>150 pS) and high degree of specificity for K$^+$ of BK channels indicates that small numbers of channels could profoundly affect membrane conductance and cell excitability. Additionally, the increase in open probability with increasing intracellular Ca$^{2+}$ indicates involvement of BK channels in the modulation of Ca$^{2+}$-dependent phenomena such as secretion and muscular contraction. [Asano, M., et al., J. Pharmacol. Exp. Ther., 267, pp.1277–1285 (1993)].

Openers of BK channels exert their cellular effects by increasing the open probability of these channels [McKay, M.C., et al., J. Neurophysiol., 71, pp.1873–1882 (1994); and Olesen, S.-P., Exp. Opin. Invest. Drugs, 3, pp.1181–1188 (1994)]. This increase in the opening of individual BK channels collectively results in the hyperpolarization of cell membranes, particularly in depolarized cells, produced by significant increases in whole-cell BK-mediated conductance.

The ability of the compound of Example 1 to open BK channels and increase whole-cell outward (K$^+$) BK-mediated currents was assessed under voltage-clamp conditions by determining their ability to increase cloned mammalian (mSlo or hSlo) BK—mediated outward current heterologously expressed in Xenopus oocytes [Butler, A., et al., Science, 261, pp. 221–224 (1993); and Dworetzky, S. I., et al., Mol. Brain Res., 27, pp.189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., J. Biol. Chem, 265, pp. 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compound profiled did not effect non-BK native currents in the oocytes. The compound of Example 1 was shown in at least 5 oocytes at a concentration of 1 μM to increase BK current to 126% of control of IBTX-sensitive current. Recordings were accomplished using standard two-electrode voltage clamp techniques [Stuhmer, W., et al., Methods in Enzymology, 207, pp. 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO$_3$ (2.4), KCl (1.0), HEPES (10), MgSO$_4$ (0.82), Ca(NO$_3$)$_2$ (0.33), CaCl$_2$ (0.41); pH 7.5.

A rapid screen to determine the ability of prodrugs to hydrolyze and release the drug (compound of Example 1) is conducted as follows. A 1 mg/mL stock solution of the prodrug is prepared in distilled water or acetonitrile or PEG-400. Plasma from freshly collected rat or human blood is used in this assay. To 1 mL of plasma at 37° C. was added 10 μL of stock solution of prodrug and mixed gently. Immediately after the mixing, 100 μL of plasma was removed and quenched with 300 μL of acetontrile (Zero time sample). Samples were also obtained at 30 minutes and quenched immediately. The quenched samples were centrifuged to obtain a clear supernatant for analysis. The stock solution, T=0 and T=30 samples were analyzed by a HPLC assay that separates the drug from the prodrug. Based on the relative peak areas of prodrug and drug in these samples, different prodrugs are characterized as fast, moderate and slow release agents. For example, in this model, the compound of Example 13 was dissolved in PEG-400 at a concentration of 1 mg/mL and incubated at 10 ug/mL in fresh rat plasma at 37° C. Analysis of the solution 5 minutes after incubation indicated conversion of the compound of Example 13 to the compound of Example 1.

To determine the ability of the compounds of the present invention to reduce cell loss resulting from neuronal ischemia, a standard focal cerebral ischemia is induced by permanent occlusion of the left middle cerebral artery (MCA) and common carotid artery (CCA) with one hour occlusion of the right CCA in the Wistar rat. The surgeries are performed using the sub-temporal approach of A. Tamura, et al., *J. Cereb. Blood Flow Metab.,* 1, pp. 53–60, (1981) and its modifications [K. Osbome, et al., *J. Neurol Neurosurg. Psychiatry,* 50, pp. 402–410 (1987) and S. Menzies, et al., *Neurosurgery,* 31, pp. 100–107, (1992).]

The compound of Example 13 was evaluated in the focal stroke model involving permanent occlusion of the left MCA (MCAO) and CCA (CCAO) and temporary occlusion of the right CCA in the Wistar rat. This procedure results in a reliably large neocortical infarct volume that is measured by means of vital dye exclusion in serial slices through the brain 24 hours after MCAO. In the present test, compounds were administered using an i.v. or i.p. route of administration two hours after occlusion. For example, in this model the compound of Example 13 significantly reduced the cortical infarct volume by about 17% when administered intravenously (1 mg/kg) as a single bolus two hours after middle cerebral artery occlusion as compared to vehicle-treated (water) control.

The results of the above in vitro and in vivo tests demonstrate that the novel 1,3,4-oxadiazol-2(3H)-one compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, sexual dysfunction, and urinary incontinence and other disorders sensitive to BK channel activating activity. Most preferably, the compounds of Formula I are useful in the treatment of cerebral ischemia/stroke.

The compounds of Formula I or pharmaceutical compositions thereof are useful in the treatment, alleviation or elimination of disorders or other disorders associated with the BK channels. Such disorders include ischemia, stroke, convulsions, epilepsy, asthma, irritable bowel syndrome, migraine, traumatic brain injury, spinal cord injury, sexual dysfunction and urinary incontinence and other disorders sensitive to potassium channel openers.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 ng/kg to 10 mg/kg body weight. For parenteral administration, the dose may be in the range of 0.1 ng/kg to 1.0 mg/kg body weight for intravenous administration. The active ingredient will preferably be administered either continuously or in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR) was recorded on a Bruker AC 300. All spectra were determined in the solvents indicated and chemical shifts are reported in 6 units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M-H)$^-$ was determined on a Finnigen TSQ 7000. High resolution mass spectra was determined on a Kratos MS50 in FAB mode using cesium iodide/glycerol as internal reference. The element analysis are reported as percent by weight.

The following examples illustrate procedures for the preparation of starting materials, intermediates and methods for the preparation of products according to this invention. It should also be evident to those skilled in the art that appropriate substitution of both materials and methods disclosed herein will produce the examples illustrated below and those encompassed by the scope of this invention.

EXAMPLE 1

3-[(5-Chloro-2-hydroxyphenyl)methyl]-5-[4-(trifluoromethyl)phenyl]-1,3,4-oxadiazol-2(3H)-one Step A 5-[4-(Trifluoromethyl)phenyl]-1,3,4-oxadiazol-2(3H)-one 4-(Trifluoromethyl)benzoic acid hydrazide (commercially available from Maybridge Chemicals) (5 g, 24.5 mmol) was taken up in THF (250 ml)/triethylamine (2.7 ml, 26 mmol) under $N_2$ and 1,1'-carbonyl-diimidazole (4.2 g, 26 mmol) added. The solution was stirred for 18 h at 24° C., concentrated, and the residue was taken up in ethyl acetate, washed with 1N HCl solution, sat'd NaHCO$_3$ solution, and brine prior to drying (MgSO$_4$). Concentration gave 5 g (89%) of the title compound from which a sample was recrystallized from diethyl ether/hexanes: mp 214–216° C. MS m/z: 231 (MH$^+$).
IR (KBr) 3280, 1778, 1608, 1420, 1318, 1170, 1114 cm$^{-1}$;
$^1$H NMR (DMSO-d$_6$) δ87.87 (2H, d, J=8.3 Hz), 7.96 (2H, d, J=8.3 Hz), 12.77 (1H, br.s);
Anal. Calcd. for C$_9$H$_5$F$_3$N$_2$O$_2$.064 H$_2$O: C, 46.74; H, 2.24; N, 12.11.
Found: C, 47.07; H, 2.10; N, 12.34.

Step B

3-[(5-Chloro-2-methoxyphenyl)methyl]-5-[4-(trifluoromethyl)-phenyl]-1,3,4-oxadiazol-2(3H)-one 5-[4-(Trifluoromethyl)phenyl]-1,3,4-oxadiazol-2(H)-one (11.75 g, 51 mmol) and 5-chloro-2-methoxybenzylbromide [N. Meanwell, et al., *Bioorg. Med. Chem. Lett.* 6, pp.1641–1646 (1996)] (12.0 g, 51 mmol) and 11.2 g (81 mmol) of potassium carbonate were added to CH$_3$CN (300 ml) under nitrogen and potassium iodide (0.2 g, 1.2 mmol) was added. The solution was refluxed for 16 h, cooled, poured into water (1500 ml) and stirred vigorously. The precipitate was filtered to give a solid which was recrystallized from CH$_3$CN to give 15.2 g (78%) of the title compound.
mp 144–145° C. MS(ESI)m/z: 385 (MH$^+$).
IR (KBr) 3440, 1782, 1492, 1324, 1248, 1168 cm$^{-1}$;
$^1$H NMR (300 MHz, DMSO) δ3.79 (3H, s), 4.91 (2H, s), 7.07 (1 H, d, J=8.8 Hz), 7.35–7.38 (2H, m), 7.88 (2H, d, J=8.4 Hz), 7.96 (2H, d, J=8.2 Hz);
Anal. Calcd. for C$_{17}$H$_{12}$ClF$_3$N$_2$O$_3$.0.1 H$_2$O: C, 52.81; H, 3.19; N, 7.25.
Found: C, 53.03; H, 3.20; N, 7.31.

Step C

3-[(5-Chloro-2-hydroxyphenyl)methyl]-5-[4-(trifluoromethyl)-phenyl]-1,3,4-oxadiazol-2(3H)-one 3-[(5-Chloro-2-methoxyphenyl)methyl]-5-[4-(trifluoromethyl)-phenyl]-1,3,4-oxadiazol-2(3H)-one (15.2 g, 39.6 mmol) was admixed with pyridine hydrochloride (19.7 g, 0.17 mol) and heated at 225° C. for 2 h. The hot solution was poured into 800 ml of 1 N HCl and the mixture was stirred for 10 min. The solid was collected, washed with 1 N HCl and dried at 80° C. under vacuum to afford 13.1 g of an off-white solid. Recrystallization from acetonitrile gave 10.8 g of the title compound as fluffy needles, mp 217–218° C. MS m/z: 371 (MH$^+$).
IR (KBr) 3354, 1762, 1500, 1324, 1068 cm$^{-1}$;
$^1$H NMR (DMSO-d$_6$) δ4.98 (2H, s), 6.84 (1 H, d, J=8.7 Hz), 7.20 (1 H, dd, J=8.7 Hz, 2.6 Hz), 7.30 (1H, d, J=2.5 Hz), 7.89 (2H, d, J=8.6 Hz), 7.97 (1H, d, J=8.6 Hz), 10.11 (1H, br.s);
Anal. Calcd. for C$_{16}$H$_{10}$ClF$_3$N$_2$O$_3$: C, 51.84; H, 2.72; N, 7.56.
Found: C, 51.88; H, 2.58; N, 7.57.

EXAMPLE 2

3-[[5-Chloro-2-[[[[2-(dimethylamino)ethyl]oxy]carbonyl]oxy]phenyl]methyl]-5-[4(trifluoromethyl)phenyl]-1,3,4-oxadiazol-2(3H)-one Step A 4-Chloro-2-[[5-[4-(trifluoromethyl)phenyl]-2,3-dihydro-2-oxo-1,3,4-oxadiazol-3-yl]methyl]phenyl chloroformate A stirred suspension of 3-[(5-chloro-2-hydroxyphenyl)methyl]-5-[4-(trifluoromethyl)phenyl]-1,3,4-oxadiazol-2(3H)-one (1 g, 2.69 mmol) and BnPh$_3$PCl (25 mg) in 1.9 molar toluene solution of phosgene (15 mL) was heated at 120° C. overnight in a sealed tube. After removal of excess phosgene, the toluene solution was rotary evaporated to dryness to afford the chlorotormate product as a white semi-solid (1.18 g).

Step B

3-[[5-Chloro-2-[[[[2-(dimethylamino)ethyl]oxy]carbonyl]oxy]phenyl]methyl]-5-[4-(trifluoromethyl)phenyl]-1,3,4-oxadiazol-2(3H)-one To a stirred cold (0° C.) solution of the chloroformate of Step A (0.6 g, 0.15 mmol) in anhydrous CH$_2$Cl$_2$ (5 mL), neat 2-(dimethylamino)-ethanol (0.41 g, 0.45 mmol) was added dropwise. The resultant mixture was allowed to warm to room temperature and maintained for 2–3 hrs. The CH$_2$Cl$_2$ was rotary evaporated at room temperature and the residue was partitioned between ether and 5% NaHCO$_3$. The ether layer was separated and washed with brine and then dried (MgSO$_4$). Evaporation of the solvent gave the product as a light yellow oil (0.613 g). Reaction of the crude product with anhydrous HCl in ether gave the corresponding hydrochloride salt of 3-[[5-chloro-2-[[[[2-(dimethylamino)ethyl]oxy]-carbonyl]oxy]phenyl]methyl]-5-[4-(trifluoromethyl)phenyl]-1,3,4-oxadiazol-2(3H)-one.

mp 160–163° C.; MS m/z 486 (MH⁺).

EXAMPLE 3

2-[[[[4-Chloro-2-[[5-[4-(trifluoromethyl)phenyl]-2,3-dihydro-2-oxo-1,3,4-oxadiazol-3-yl]methyl]phenoxy]carbonyl]oxy]ethyl]trimethylammonium methanesulfonate The crude 3-[[5-chloro-2-[[[[2-(dimethylamino)ethyl]oxy]carbonyl]oxy]phenyl]methyl]-5-[4-(trifluoromethyl)phenyl]-1,3,4-oxadiazol-2(3H)-one was dissolved 1:1 ether-EtOAc and neat methyl methanesulfonate (2 eqt.) was added. The mixture was stirred at room temperature overnight. The precipitated solid was collected by filtration, washed with ether and then dried in vacuo to afford the title compound as a white solid:
mp 190–195° C. (dec.);
IR (KBr, cm$^{-1}$) 1193, 1318, 1765, 1777;
$^1$H NMR (CDCl$_3$) δ2.76 (s, 3H), 3.51 (s, 9H), 4.19 (m, 2H), 4.75 (m, 2H), 4.89 (s, 2H), 7.17 (d, J=8.6 Hz, 1H), 7.25 (s, 1H), 7.38 (dd, J=8.6 and 2.5 Hz, 1H), 7.54 (d, J2.5 Hz, 1H), 7.71 (d, J =8.4 Hz, 1H), 7.91 (d, J=8.1 Hz, 1H); MS m/z 500 (M⁺).

General procedure for the preparation of Examples 4–11

The following describes the general procedure used for the preparation of compounds of the Formula VIIa–c and VIIIa–c which is also illustrated herein in Reaction Scheme 2. The acid chlorides of Formula VIa–c were prepared by reacting the corresponding acids with oxalyl chloride and a catalytic amount of DMF in CH$_2$Cl$_2$. The acid chlorides of Formula VIa–c were isolated as HCl salt and used without further purification. To a stirred suspension of the compound of Example 1 (1 eqt.) and NaH (2 eqt.) in anhydrous ether, the corresponding acid chloride of Formula VI (1.2 eqt.) was added and the mixture was stirred for 3–4 hrs. The reaction mixture was diluted with ether and EtOAc, washed with 5% NaHCO$_3$, water, brine and then dried (MgSO$_4$). The solvents were rotary evaporated and the residue was recrystallized from ether-hexanes to provide the compound of Formula VIIa–c. Neat methyl methanesulfonate was added to a solution of a compound of Formula VIIa–c in 1:1 ether-EtOAc and the mixture was stirred at room temperature overnight. The precipitated white solid was filtered, washed 15 with ether and then dried in vacuo to afford the corresponding pure compound of Formula VIIIa–c.

EXAMPLE 4

4-Chloro-2-[[5-[4-(trifluoromethyl)phenyl]-2,3-dihydro-2-oxo-1,3,4-oxadiazol-3-yl]methyl]phenyl (dimethylamino)acetate (VIIa, n=1)

mp 112–113° C.; MS m/z: 456 (MH⁺).
Anal. Calcd. for C$_{20}$H$_{17}$ClF$_3$N$_3$O$_4$: C, 52.70; H, 3.76; N, 9.22.
Found: C, 52.51; H, 3.66; N, 9.10.

EXAMPLE 5

4-Chloro-2-[[5-(trifluoromethyl)phenyl]-2,3-dihydro-2-oxo-1,3,4-oxadiazol-3-yl]methyl]phenyl-3-(diethylamino)propionate (VIIb, n=2)

mp 179–181° C.; MS m/z: 498 (MH⁺).
Anal. Calcd. for C$_{23}$H$_{23}$ClF$_3$N$_3$O$_4$.HCl: C, 51.70; H, 4.53; N, 7.86.
Found: C, 51.46; H, 4.67; N, 7.71.

EXAMPLE 6

4-Chloro-2-[[5-[4-(trifluoromethyl)phenyl]-2,3-dihydro-2-oxo-1,3,4-oxadiazol-3-yl]methyl]phenyl-4-(dimethylamino)butyrate (VIIc, n=3)

mp 162–164° C.;
Anal. Calcd. for C$_{22}$H$_{21}$ClF$_3$N$_3$O$_4$.HCl: C, 50.78; H, 4.26; N, 8.08.
Found: C, 49.51; H, 4.35; N, 7.80.

EXAMPLE 7

[[[4-Chloro-2-[[5-[4-(trifluoromethyl)phenyl]-2,3-dihydro-2-oxo-1,3,4-oxadiazol-3-yl]methyl]phenoxy]carbonyl]methyl]-trimethylammonium methanesulfonate (VIIIa, n=1)

mp 230–232° C.; MS m/z: 470 (M⁺).
Anal. Calcd. for C$_{21}$H$_{20}$ClF$_3$N$_3$O$_4$.CH$_3$SO$_3$: C, 46.69; H, 4.10; N, 7.42.
Found: C, 46.06; H, 4.06; N, 7.21.

EXAMPLE 8

2-[[[4-Chloro-2-[5-[4-(trifluoromethyl)phenyl]-2,3-dihydro-2-oxo-1,3,4-oxadiazol-3-yl]methyl]phenoxy]carbonyl]ethyl]-diethylmethylammonium methanesulfonate (VIIIb, n=2)

mp>260° C.

EXAMPLE 9

3-[[[4-Chloro-2-[[5-[4-(trifluoromethyl)phenyl]-2,3-dihydro-2-oxo-1,3,4-oxadiazol-3-yl]methyl]phenoxy]carbonyl]propyl]trimethylammonium methanesulfonate (VIIIc, n=3)

mp>260° C.; MS m/z: 498 (M⁺).
Anal. Calcd. for C$_{23}$H$_{24}$ClF$_3$N$_3$O$_4$.CH$_3$SO$_3$: C, 48.53; H, 4.58; N, 7.07.
Found: C, 48.61; H, 4.58; N, 7.03.

EXAMPLE 10

4-Chloro-2-[[5-[4-trifluoromethyl)phenyl]-2,3-dihydro-2-oxo-1,3,4-oxadiazol-3-yl]methyl]phenyl (methylamino)acetate mp 186–188° C. (dec.).

EXAMPLE 11

4-Chloro-2-[[5-[4-(trifluoromethyl)phenyl]-2,3-dihydro-2-oxo-1,3,4-oxadiazol-3-yl]methyl]phenyl-3-aminopropionate mp 184–185° C. (dec.).

EXAMPLE 12

[4-Chloro-2-[[5-[4-(trifluoromethyl)phenyl]-2,3-dihydro-2-oxo-1,3,4-oxadiazol-3-yl]methyl]phenoxy]methyl-4-dimethylamino)butyrate (XIc, n=3)

Step A

3-[[5-Chloro-2-(methylthiomethoxy)phenyl]methyl]-5-[4-(trifluoromethyl)phenyl]-1,3,4-oxadiazol-2(3H)-one (IX)

A solution of 3-[(5-chloro-2-hydroxyphenyl)methyl]-5-[4-(trifluoromethyl)phenyl]-1,3,4-oxadiazol-2(3H)-one (6.0 g, 16.2 mmol) in dry HMPA (50 mL) was added dropwise under nitrogen to a stirred suspension of sodium hydride (0.77 g of 60% dispersion in mineral oil, 19.4 mmol) in HMPA (15 mL). The resultant yellow solution was stirred for 30 min and then neat chloromethyl methyl sulfide (1.49 mL, 17.8 mmol) was added dropwise. The reaction mixture was stirred at room temperature overnight and the product was extracted with ethyl acetate (500 mL). The EtOAc layer was washed with satd. $NaHCO_3$, water, brine and then dried ($MgSO_4$). Rotary evaporation of EtOAc gave a yellow semi-solid which was recrystallized from ethyl acetate/hexanes to afford the title compound as white crystals (4.4 g, 70%).

$^1$H NMR ($CDCl_3$) δ2.28 (s, 3H), 5.00 (s, 2H), 5.22 (s, 2H), 6.92 (d, J=8.5 Hz, 1H), 7.3 (m, 2H), 7.74 (d, J=8.4 Hz, 2H), 7.96 (d, J=8.3 Hz, 2H).
IR (KBr, cm$^{-1}$): 1779, 1608, 1494, 1328, 1238, 1176, 1126.
Anal. Calcd. for $C_{18}H_{14}ClF_3N_2O_3S$: C, 50.18; H, 3.28; N, 6.50.
Found: C, 50.19; H, 3.32; N, 6.52.

Step B

3-[[5-Chloro-2-(chloromethoxy)phenyl]methyl]-5-[4-(trifluoromethyl)phenyl-1,3,4-oxadiazol-2(3H)-one (X)

Neat sulfuryl chloride (0.78 mL, 9.75 mmol) was added dropwise to a stirred solution of the compound from Step A (3.5 g, 8.12 mmol) in $CH_2Cl_2$ (40 mL) under nitrogen. The reaction mixture was stirred at room temperature for 4 hrs. TLC indicated completion of the reaction. After removal of excess reagent and $CH_2Cl_2$ by rotary evaporation the product was dried under vacuum to afford the title compound as an off-white solid (3.4 g,100%).
MS m/z: 419 (MH$^+$).
$^1$H NMR ($CDCl_3$) δ5.0 (s, 2H), 5,94 (s, 2H), 7.18 (d, J=9.2 Hz, 1 H), 7.38 (m, 2H), 7.74 (d, J=8.4 Hz, 2H), 7.96 (d, J=8.3 Hz, 2H).
IR (KBr, cm$^{-1}$): 1773, 1611, 1572, 1487, 1325, 1163, 1128.
Anal. Calcd. for $C_{17}H_{11}Cl_2F_3N_2O_3$.0.25 $H_2O$: C, 48.19; H, 2.76; N, 6.61.
Found: C, 48.04; H, 2.68; N, 6.53.

Step C

[4-Chloro-2-[[5-[4-(trifluoromethyl)phenyl]-2,3-dihydro-2-oxo-1,3,4-oxadiazol-3-yl]methyl]phenoxy]methyl-4-(dimethylamino)butyrate (XIc, n=3)

The chloromethoxy compound of Step B (0.8 g, 1.91 mmol) was added to a stirred suspension of $Cs_2CO_3$ (1.306g, 4.01 mmol) and 4-(dimethylamino)butyric acid hydrochloride (0.352 g, 2.1 mmol) in acetone (20 mL). The reaction mixture was stirred at room temperature overnight. TLC indicated completion of the reaction. Acetone was rotary evaporated and brine solution was added. The yellow precipitate was collected by filtration and washed with water and then air dried. The crude solid was recrystallized from ethyl acetate/hexanes to afford the title compound XIc as a white solid (0.64 g, 65%).
mp 115–117° C.;
$^1$H NMR (DMSO-$d_6$) δ1.49 (m, 2H), 2.02 (t, J=7.0 Hz, 2H), 2.25 (t, J=7.3 Hz, 2H), 3.32 (s, 6H), 4.92 (s, 2H), 5.79 (s, 2H), 7.24 (d, J=8.8 Hz, 1H), 7.43 (dd, J=2.6 Hz, 8.8 Hz, 1H), 7.50 (d, J=2.6 Hz, 1H), 7.90 (d, J=8.5 Hz, 2H), 7.98 (d, J=8.3 Hz, 2H).
IR (KBr, cm$^{-1}$): 1776, 1764, 1607, 1492, 1416, 1324, 1121.
Anal. Calcd. for $C_{23}H_{23}ClF_3N_3O_5$.0.5 $H_2O$: C, 52.83; H, 4.63; N, 8.04.
Found: C, 53.00; H, 4.70; N, 8.04.

EXAMPLE 13

3-[[[[4-Chloro-2-[[5-[4-(trifluoromethyl)phenyl]-2,3-dihydro-2-oxo -1,3,4oxadiazol-3-yl]methyl]phenoxy]methoxy]carbonyl]propyl]trimethylammonium methanesulfonate (XIIc, n=3)

The compound of Example 12 (XIc) (0.95 g,1.85 mmol) was dissolved in ethyl acetate (10 mL) and neat methyl methanesulfonate (0.32 mL, 3.7 mmol) was added dropwise. The reaction mixture was stirred at room temperature overnight. The white precipitate was collected and purified by trituration with ether to afford the title compound as a white solid (0.95 g, 82%). Recrystallization from ethanol/ether gave white crystals:
mp 156–158° C.; MS m/z: 528 (MH$^+$).
$^1$H NMR (DMSO-$d_6$) δ1.91 (m, 2H), 2.27 (s, 3H), 2.43 (t, J=7.1 Hz, 2H), 3.01 (s, 9H), 3.22(m, 2H), 4.91 (s, 2H), 5.81 (s, 2H), 7.24 (d, J=8.9 Hz, 1H), 7.43 (dd, J=2.7 Hz, 8.8 Hz, 1H), 7.49 (d, J=2.6 Hz, 1H), 7.90 (d, J=8.5 Hz, 2H), 7.98 (d, J=8.4 Hz, 2H);
Anal. Calcd. for $C_{24}H_{26}ClF_3N_3O_5.CH_3SO_3$: C, 48.12; H, 4.68; N, 6.73.
Found: C, 48.15; H, 4.74; N, 6.71.

EXAMPLE 14

[[[[4-Chloro-2-[[5-[4-(trifluoromethyl)phenyl]-2,3-dihydro-2-oxo-1,3,4-oxadiazol-3-yl]methyl]phenoxy]methoxy]carbonyl]methyl]trimethylammonium methanesulfonate (XIIa, n=1)

To a mixture of compound X from Example 12, Step B (0.4 g, 0.95 mmol), $Cs_2CO_3$ (0.342 g, 1.05 mmol) and N,N-dimethylglycine (0.108 g, 1.05 mmol), acetone (20 mL) was added. The reaction mixture was stirred at room temperature overnight. Acetone was rotary evaporated and then brine was added. The white precipitate of compound XIa (n=1) was collected and dissolved in acetonitrile and neat methyl methanesulfonate (0.053 mL) was added. The reaction mixture was stirred at room temperature for 2 days. The solvent was evaporated and ether was added. The precipitate was collected and purified by recrystallization from acetonitrile/ether to afford the title compound as a white solid (0.13 g, 23% two steps). mp: 100–104° C. MS m/z: 500 (M$^+$).
$^1$H NMR (DMSO-$d_6$) δ2.27 (s, 3H), 3.33 (s, 9H), 4.60 (s, 2H), 5.09 (s, 2H), 5.48 (s, 2H), 7.24 (d, J=8.9 Hz, 1H), 7.52 (dd, J=2.6 Hz, 8.8 Hz, 1H), 7.60 (d, J=2.6 Hz, 1H), 7.90 (d, J=8.6 Hz, 2H), 7.97 (d, J=8.3 Hz, 2H).
Anal. Calcd. for $C_{22}H_{22}ClF_3N_3O_5.CH_3SO_3.1.5$ $H_2O$: C, 44.34; H, 4.53; N, 6.74.

Found: C, 44.35; H, 4.28; N, 6.46.

EXAMPLE 15

[4-Chloro-2-[[5-[4-(trifluoromethyl)phenyl]-2,3-dihydro-2-oxo-1,3,4-oxadiazol-3-yl]methyl]phenoxy]methyl-3-(diethylamino)propionate hydrochloride (XIb, n=2)

To a mixture of compound X from Example 12, Step B, (0.4 g, 0.95 mmol), $Cs_2CO_3$ (0.622 g, 1.91 mmol) and 3-(diethylamino)propionic acid hydrochloride (0.108 g, 1.05 mmol), acetone (20 mL) was added. The reaction mixture was stirred at room temperature for 3 days. Acetone was rotary evaporated and brine was added to the residue. The precipitated white solid (0.38 g, 75%) was collected. To a stirred solution of crude product (0.16 g, 0.30 mmol) in ethyl acetate 1N HCl in ether (0.36 mL, 0.36 mmol) was added and kept at room temperature for 3 hr. The hydrochloride salt of the title compound XIb was collected by filtration (0.11 g, 64%):

mp 165–167° C. (dec.); MS m/z: 528 (MH$^+$).

$^1$H NMR (DMSO-d$_6$) δ1.16 (t, J=7.2 Hz, 6H), 2.93 (t, J=7.8 Hz, 2H), 3.01–3.10 (m, 4H), 3.19–3.25 (m, 2H), 4.93 (s, 2H), 5.84 (s, 2H), 7.27 (d, J=8.8 Hz,1H), 7.44 (dd, J=2.6 Hz, 8.8 Hz, 1H), 7.51 (d, J=2.6 Hz, 1H), 7.91 (d, J=8.5 Hz, 2H), 8.00 (d, J=8.3 Hz, 2H), 10.5 (s, br, 1H).

Anal. Calcd. for $C_{24}H_{25}ClF_3N_3O_5 \cdot HCl$: C, 51.08; H, 4.64; N, 7.45.

Found: C, 46.94; H, 4.42; N, 6.76.

EXAMPLE 16

3-[[[[4-Chloro-2-[[5-[4-(trifluoromethyl)phenyl]-2,3-dihydro-2-oxo-1,3,4-oxadiazol-3-yl]methyl]phenoxy]methoxy]carbonyl]-2-hydroxypropyl]trimethylammonium methanesulfonate (XIII)

To a stirred suspension of compound X from Example 12, Step B (0.4 g, 0.95 mmol) and $Cs_2CO_3$ (0.342 g, 1.05 mmol) in acetone (20 mL), (L)-norcamitine [Colucci, W. J.; Tumbull, Jr., S. P.; Gandour, R. D.; *Analytical Biochemistry*, 162, pp.459–462 (1987)] (0.155 g, 1.05 mmol) was added. The reaction mixture was stirred at room temperature for 2 hr. Acetone was rotary evaporated and water was added and then extracted with ether. The extract was then washed with water, brine and dried (MgSO$_4$). Evaporation of ether gave a yellowish foamy solid which was 15 then dissolved in ether and 0.1 mL of methyl methanesulfonate was added. The reaction mixture was stirred at room temperature overnight. The precipitated solid was collected and triturated with ethyl acetate/ether to afford the title compound as an off-white solid (0.2 g, 33% two steps). mp: 98–101° C. MS m/z: 544 (M$^+$).

$^1$H NMR (DMSO-d$_6$) δ2.30 (s, 3H), 2.52-2.58 (m, 2H), 3.10 (s, 9H), 3.34–3.41 (m, 2H), 4.43 (m, 1H), 4.94 (s, 2H), 5.73 (d, J=6.2 Hz, 1H), 5.81 (d. J=5.5 Hz, 1H), 5.84 (d, J=6.6 Hz, 1H), 7.27 (d, J=8.8 Hz, 1H), 7.44 (dd, J=2.7 Hz, 8.8 Hz, 1H), 7.49 (d, J=2.6 Hz, 1H), 7.91 (d, J=8.5 Hz, 2H), 7.99 (d, J=8.3 Hz, 2H);

IR (KBr, cm$^{-1}$): 3307, 1784, 1751, 1490, 1417, 1324, 1194, 1123, 1065.

Anal. Calcd. for $C_{24}H_{26}ClF_3N_3O_6 \cdot CH_3SO_3 \cdot 0.75\ H_2O$: C, 45.95; H, 4.70; N, 6.43.

Found: C, 45.88; H, 4.69; N, 6.13.

EXAMPLE 17

2-[[[[4-Chloro-2-[[5-[4-(trifluoromethyl)phenyl]-2,3-dihydro-2-oxo-1,3,4-oxadiazol-3-yl]methyl]phenoxy]methoxy]carbonyl]oxy]ethyl]trimethylammonium methanesulfonate (XVIIa, n=1)

Step A

3-[[2-[[[(Butylthio)carbonyl]oxy]methoxy]-5-Chlorophenyl]methyl]-5-[4-(trifluoromethyl)phenyl]-1,3,4-oxadiazol-2(3H)-one (XIV)

Sodium hydride (60% in mineral oil, 144 mg, 3.6 mmol) was added to stirred cold (0° C.) solution of the compound of Formula II (1.11 g, 3 mmol) in dry HMPA (6 mL) under nitrogen and then allowed to warm to room temperature. After 30 min. the resultant yellow solution was cooled to 0° C. and then neat O-iodomethyl-S-butyl carbonothioate [Folkman, M. and Lund, F., *Synthesis*, pp.1159, (1990)] (1.0 g, 3.6 mmol) was added dropwise. The resultant mixture was allowed to warm to room temperature and stirred overnight. Saturated brine was added to the reaction mixture and the precipitated white solid was filtered, washed thoroughly with water. The crude wet solid was dissolved in 1:1:1 EtOAc-CH$_2$Cl$_2$-THF and then dried (MgSO$_4$). Filtration and evaporation of solvents gave a white solid (1.76 g) which was recrystallized from ether to afford pure XIV (693 mg, 62%).

Step B

[4-Chloro-2-[[5-[4-(trifluoromethyl)phenyl]-2,3-dihydro-2-oxo-1,3,4-oxadiazol-3-yl]methyl]phenoxy]methyl chloroformate (XV)

Neat sulfuryl chloride (80 µL, 1 mmol) was added to a stirred solution of the compound of Step A (258 mg, 0.5 mmol) in anhydrous CH$_2$Cl$_2$ (2 mL) under nitrogen. The resultant mixture was stirred at room temperature for 2 hrs. The reaction mixture was rotary evaporated to dryness at room temperature and then kept under high vacuum to afford the desired chloroformate of Formula XV as a white solid (0.23 g).

Step C

3-[[5-Chloro-2-[[[[2-(dimethylamino)ethyl]oxy]carbonyl]oxy]methoxy]phenyl]methyl]-5-[4-(trifluoromethyl)phenyl]-1,3,4-oxadiazol-2(3H)-one (XVIa, n=1)

Neat dry 2-(dimethylamino)ethanol (134 mg) was added to a stirred solution of the compound of Formula XV from Step B (0.23 g) in anhydrous CH$_2$Cl$_2$ (5 mL) and the mixture stirred overnight. Reaction mixture was diluted with CH$_2$Cl$_2$ and then quenched with 5% NaHCO$_3$. Organic layer was separated and washed with water, brine and then dried (MgSO$_4$). Evaporation of CH$_2$Cl$_2$ gave the title compound as a light yellow oil (0.21 g).

Step D

2-[[[[4-Chloro-2-[[5-[4-(trifluoromethyl)phenyl]-2,3-dihydro-2-oxo-1,3,4-oxadiazol-3-yl]methyl]phenox]methoxy]-carbonyl]oxy] ethyl] trimethylammonium methanesulfonate (XVIIa, n=1)

The crude product from Step C (0.2 g) was dissolved in 1:1 ether-EtOAc (5 mL) and treated with methyl methanesulfonate (2 eqt.). The mixture was stirred at room temperature overnight and the precipitated white solid was filtered, washed with ether and then dried in vacuo to afford the title compound as a white solid (94 mg):

mp 145–150° C. (dec.);

$^1$H NMR (CDCl$_3$) δ2.76 (s, 3H), 3.45 (s, 9H), 4.16 (m, 2H), 4.71 (m, 2H), 4.96 (s, 2H), 5.79 (s, 2H), 6.98 (d, J=8.4 Hz, 1H), 7.31–7.34 (m, 2H), 7.75 (d, J=8.4 Hz, 2H), 7.97 (d, J=8.2 Hz, 2H); MS m/z 530 (M$^+$).

What is claimed:

1. A compound of the formula

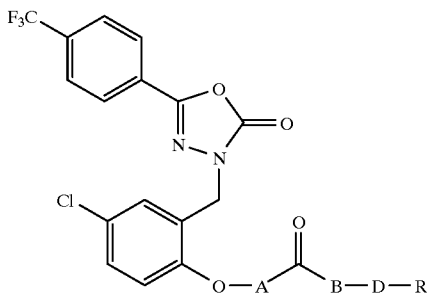

wherein

A is a direct bond or —CH$_2$O—;

B is a direct bond or oxygen;

D is —(CH$_2$)$_n$— or —CH$_2$CHOHCH$_2$—;

n is an integer from 1 to 4;

R is —NR$^1$R$^2$ or

in which

is a counter anion; and

R$^1$, R$^2$, and R$^3$ each are independently hydrogen or C$_{1-4}$ alkyl; or a nontoxic pharmaceutically acceptable salt or solvate thereof.

2. The compound of claim 1 wherein A is a direct bond, B is a direct bond, and D is —(CH$_2$)$_n$—.

3. The compound of claim 2 selected from the group consisting of:

4-chloro-2-[[5-[4-(trifluoromethyl)phenyl]-2,3-dihydro-2-oxo-1,3,4-oxadiazol-3-yl]methyl]phenyl (dimethylamino)acetate;

4-chloro-2-[[5-[4-(trifluoromethyl)phenyl]-2,3-dihydro-2-oxo-1,3,4-oxadiazol-3-yl]methyl]phenyl-3-(diethylamino)propionate;

4-chloro-2-[[5-[4-(trifluoromethyl)phenyl]-2,3-dihydro-2-oxo-1,3,4-oxadiazol-3-yl]methyl]phenyl-4-(dimethylamino)butyrate;

[[[4-chloro-2-[[5-[4-(trifluoromethyl)phenyl]-2,3-dihydro-2-oxo-1,3,4-oxadiazol-3-yl]methyl]phenoxy]carbonyl]methyl]trimethylammonium methanesulfonate;

2-[[[4-chloro-2-[[5-[4-(trifluoromethyl)phenyl]-2,3-dihydro-2-oxo-1,3,4-oxadiazol-3-yl]methyl]phenoxy]carbonyl]ethyl]diethylmethylammonium methanesulfonate;

3-[[[4-chloro-2-[[5-[4-(trifluoromethyl)phenyl]-2,3-dihydro-2-oxo-1,3,4-oxadiazol-3-yl]methyl]phenoxy]carbonyl]propyl]trimethylammonium methanesulfonate;

4-chloro-2-[[5-[4-(trifluoromethyl)phenyl]-2,3-dihydro-2-oxo-1,3,4-oxadiazol-3-yl]methyl]phenyl (methylamino)acetate; and 4-chloro-2-[[5-[4-(trifluoromethyl)phenyl]-2,3-dihydro-2-oxo-1,3,4-oxadiazol-3-yl]methyl]phenyl-3-aminopropionate;

or a nontoxic pharmaceutically acceptable salt, counter anion or solvate thereof.

4. The compound of claim 1 wherein A is a direct bond, B is oxygen and D is —(CH$_2$)$_n$—.

5. The compound of claim 4 selected from the group consisting of:

3-[[5-chloro-2-[[[[2-(dimethylamino)ethyl]oxy]carbonyl]oxy]phenyl]methyl]-5-[4-(trifluoromethyl)phenyl]-1,3,4-oxadiazol-2(3H)-one; and 2-[[[[4-chloro-2-[[5-[4-(trifluoromethyl)phenyl]-2,3-dihydro-2-oxo-1,3,4-oxadiazol-3-yl]methyl]phenoxy]carbonyl]oxy]ethyl]trimethylammonium methanesulfonate;

or a nontoxic pharmaceutically acceptable salt, counter anion or solvate thereof.

6. The compound of claim 1 wherein A is —CH$_2$O—, B is a direct bond and D is —(CH$_2$)$_n$—.

7. The compound of claim 6 selected from the group consisting of

[4-chloro-2-[[5-[4-(trifluoromethyl)phenyl]-2,3-dihydro-2-oxo-1,3,4-oxadiazol-3-yl]methyl]phenoxy]methyl-4-(dimethylamino)butyrate;

3-[[[[4-chloro-2-[[5-[4-(trifluoromethyl)phenyl]-2,3-dihydro-2-oxo-1,3,4-oxadiazol-3-yl]methyl]phenoxy]methoxy]carbonyl]propyl] trimethylammonium methanesulfonate;

[[[[4-chloro-2-[[5-[4-(trifluoromethyl)phenyl]-2,3-dihydro-2-oxo-1,3,4-oxadiazol-3-yl]methyl]phenoxy]methoxy]carbonyl]methyl] trimethylammonium methanesulfonate; and

[4-chloro-2-[[5-[4-(trifluoromethyl)phenyl]-2-oxo-1,3,4-oxadiazol-3-yl]methyl]phenoxy]methyl-3-(diethylamino)propionate hydrochloride;

or a nontoxic pharmaceutically acceptable salt, counter anion or solvate thereof.

8. The compound of claim 7 which is 3-[[[[4-chloro-2-[[5-[4-trifluoromethyl)phenyl]-2,3-dihydro-2-oxo-1,3,4-oxadiazol-3-yl]methyl]phenoxy]methoxy]carbonyl]propyl] trimethylammonium methanesulfonate.

9. The compound of claim 1 wherein A is —CH$_2$O—, B is a direct bond and D is —CH$_2$CHOHCH$_2$—.

10. The compound of claim 9 which is 3-[[[[4-chloro-2-[[5-[4-(trifluoromethyl)phenyl]-2,3-dihydro-2-oxo-1,3,4-oxadiazol-3-yl]methyl]phenoxy]methoxy]carbonyl]-2-hydroxypropyl] trimethylammonium methanesulfonate.

11. The compound of claim 1 wherein A is —CH$_2$O—, B is oxygen, and D is —(CH$_2$)$_n$—.

12. The compound of claim 11 which is 2-[[[[[4-chloro-2-[[5-[4-(trifluoromethyl)phenyl]-2,3-dihydro-2-oxo-1,3,4-oxadiazol-3-yl]methyl]phenoxy]methoxy]carbonyl]oxy]ethyl]trimethylammonium methanesulfonate.

13. A pharmaceutical composition for the treatment of disorders responsive to openers of the large conductance calcium-activated potassium channels comprising a therapeutically effective amount of a compound as defined in claim 1 in association with a pharmaceutically acceptable carrier or diluent.

14. A method for the treatment of disorders responsive to opening of the large conductance calcium-activated potassium channels in a mammal in need thereof, which comprises administering to said mammal a therapeutically effective amount of a compound as defined in claim 1.

15. The method of claim 14 wherein said disorder is ischemia, stroke, convulsions, epilepsy, asthma, irritable bowel syndrome, migraine, traumatic brain injury, spinal cord injury, sexual dysfunction and urinary incontinence.

16. The method of claim 15 wherein the disorder is stroke.

* * * * *